US008870844B2

(12) United States Patent
Perovitch et al.

(10) Patent No.: US 8,870,844 B2
(45) Date of Patent: Oct. 28, 2014

(54) DEVICE FOR CONSERVING, EXTEMPORANEOUSLY PREPARING, AND ADMINISTERING AN ACTIVE PRINCIPLE

(76) Inventors: Philippe Perovitch, Le Temple (FR); Tatiana Galperine, Paris (FR)

( * ) Notice: Subject to any disclaimer, the term of this patent is extended or adjusted under 35 U.S.C. 154(b) by 391 days.

(21) Appl. No.: 12/937,748

(22) PCT Filed: Apr. 17, 2009

(86) PCT No.: PCT/FR2009/050721

§ 371 (c)(1),
(2), (4) Date: Oct. 14, 2010

(87) PCT Pub. No.: WO2009/138644

PCT Pub. Date: Nov. 19, 2009

(65) Prior Publication Data

US 2011/0054437 A1 Mar. 3, 2011

(30) Foreign Application Priority Data

Apr. 17, 2008 (FR) ..................................... 08 52608

(51) Int. Cl.

| | |
|---|---|
| ***A61M 5/32*** | (2006.01) |
| ***B65D 51/28*** | (2006.01) |
| *A61J 1/06* | (2006.01) |
| *A61J 1/20* | (2006.01) |

(52) U.S. Cl.

CPC ........... *A61J 1/2093* (2013.01); *B65D 51/2835* (2013.01); *A61J 1/065* (2013.01); *A61J 2001/2086* (2013.01); *A61J 1/2096* (2013.01); *A61J 2001/2027* (2013.01)

USPC .......................................................... 604/411

(58) Field of Classification Search

USPC .......................................................... 604/411

See application file for complete search history.

(56) References Cited

U.S. PATENT DOCUMENTS

| | | | | |
|---|---|---|---|---|
| 2,275,567 | A * | 3/1942 | Smith | 604/416 |
| 2,495,942 | A * | 1/1950 | Nosik | 604/416 |
| 2,631,521 | A * | 3/1953 | Atkins, Jr. | 99/275 |
| 2,721,552 | A * | 10/1955 | Nosik | 206/222 |

(Continued)

FOREIGN PATENT DOCUMENTS

| | | |
|---|---|---|
| GB | 676492 | 7/1952 |
| GB | 1083335 | 9/1967 |

*Primary Examiner* — Susan Su
*Assistant Examiner* — Guy K Townsend
(74) *Attorney, Agent, or Firm* — Sughrue Mion, PLLC

(57) ABSTRACT

The invention provides a device (10) for conserving and extemporaneously preparing at least one active principle prior to administration, the device comprising: a body (12) that is constituted by at least one compartment for containing at least one volume of pharmaceutical solvent (22) that is less than 5 mL; a head (14) constituted by at least one compartment for containing at least one active principle (24), in particular a very small dose, and, in its top portion, by at least one dose-taking chamber (32) provided with a filter (40), the head (14) being capable of taking up a first position P1 for conservation, in which said head (14) is in its distal position relative to the body (12), and a second position P2 for preparation, in which said head (14) is in its proximal position relative to the body (12); at least one wall (16) separating the body (12) and the head (14); and rupture means (18) for rupturing said wall (16) so that the active principle (24) enters into contact with the solvent (22) and dissolves therein. The invention also seeks to use the device for conserving and extemporaneously preparing at least one active principle with a view to administering it.

20 Claims, 4 Drawing Sheets

(56) References Cited

U.S. PATENT DOCUMENTS

| | | | | | |
|---|---|---|---|---|---|
| 2,773,591 | A * | 12/1956 | Jensen | 206/220 |
| 3,441,179 | A * | 4/1969 | Ragan | 222/129 |
| 3,467,282 | A * | 9/1969 | Schwartzman | 222/94 |
| 3,731,853 | A * | 5/1973 | Baumann et al. | 222/386 |
| 3,739,947 | A * | 6/1973 | Baumann et al. | 222/136 |
| 3,924,741 | A * | 12/1975 | Kachur et al. | 206/221 |
| 4,024,952 | A * | 5/1977 | Leitz | 206/221 |
| 4,136,775 | A * | 1/1979 | Zaltsman | 206/219 |
| 4,386,696 | A * | 6/1983 | Goncalves | 206/221 |
| 4,615,437 | A * | 10/1986 | Finke et al. | 206/222 |
| 4,638,927 | A * | 1/1987 | Morane | 222/83 |
| 4,903,865 | A * | 2/1990 | Janowitz | 222/83.5 |
| 4,982,875 | A * | 1/1991 | Pozzi et al. | 222/83 |
| 5,000,314 | A * | 3/1991 | Fuller et al. | 206/221 |
| 5,217,433 | A * | 6/1993 | Bunin | 604/89 |
| 5,388,690 | A | 2/1995 | Mutterle et al. | |
| 5,772,017 | A * | 6/1998 | Kang | 206/222 |
| 5,927,549 | A * | 7/1999 | Wood | 222/83 |
| 5,941,380 | A * | 8/1999 | Rothman | 206/222 |
| 5,944,175 | A * | 8/1999 | Albisetti | 206/221 |
| 5,950,819 | A * | 9/1999 | Sellars | 206/221 |
| 5,967,309 | A * | 10/1999 | Robles-Gonzalez et al. | 206/221 |
| 6,003,728 | A * | 12/1999 | Elliott | 222/81 |
| 6,098,795 | A * | 8/2000 | Mollstam et al. | 206/222 |
| 6,138,821 | A * | 10/2000 | Hsu | 206/222 |
| 6,148,996 | A * | 11/2000 | Morini | 206/222 |
| 6,230,884 | B1 * | 5/2001 | Coory | 206/222 |
| 6,244,433 | B1 * | 6/2001 | Vieu | 206/221 |
| 6,247,586 | B1 * | 6/2001 | Herzog et al. | 206/221 |
| 6,378,714 | B1 * | 4/2002 | Jansen et al. | 215/249 |
| 6,387,073 | B1 | 5/2002 | Weiler et al. | |
| 6,435,341 | B1 * | 8/2002 | Nobbio | 206/219 |
| 6,513,650 | B2 * | 2/2003 | Mollstam et al. | 206/222 |
| 6,527,110 | B2 * | 3/2003 | Moscovitz | 206/222 |
| 6,533,113 | B2 * | 3/2003 | Moscovitz | 206/222 |
| 6,601,721 | B2 * | 8/2003 | Jansen et al. | 215/249 |
| 6,705,491 | B1 * | 3/2004 | Lizerbram et al. | 222/145.1 |
| 6,772,910 | B1 * | 8/2004 | Coory | 222/83 |
| 6,854,595 | B2 * | 2/2005 | Kiser | 206/222 |
| 6,921,087 | B2 * | 7/2005 | Takahashi et al. | 277/628 |
| 6,926,138 | B1 * | 8/2005 | Basham et al. | 206/222 |
| 7,017,735 | B2 * | 3/2006 | Carlson | 206/222 |
| 7,032,745 | B2 * | 4/2006 | Saulle | 206/219 |
| 7,083,803 | B2 * | 8/2006 | Peyman | 424/422 |
| 7,249,690 | B2 * | 7/2007 | Smith et al. | 222/83 |
| 7,308,915 | B2 * | 12/2007 | Johns et al. | 141/100 |
| 7,503,453 | B2 * | 3/2009 | Cronin et al. | 206/221 |
| 2002/0040856 | A1 * | 4/2002 | Mollstam et al. | 206/222 |
| 2002/0066748 | A1 * | 6/2002 | Weiler et al. | 222/129 |
| 2002/0079285 | A1 * | 6/2002 | Jansen et al. | 215/249 |
| 2004/0112770 | A1 * | 6/2004 | Oswald | 206/219 |
| 2004/0200740 | A1 * | 10/2004 | Cho | 206/219 |
| 2004/0200741 | A1 * | 10/2004 | Cho | 206/219 |
| 2005/0115845 | A1 * | 6/2005 | Cho | 206/216 |
| 2005/0173271 | A1 * | 8/2005 | Levi | 206/219 |
| 2005/0236424 | A1 * | 10/2005 | Walters et al. | 222/83 |
| 2006/0006077 | A1 * | 1/2006 | Mosher et al. | 206/219 |
| 2007/0160648 | A1 * | 7/2007 | Ashton et al. | 424/426 |
| 2008/0208159 | A1 * | 8/2008 | Stanus et al. | 604/408 |

* cited by examiner

DEVICE FOR CONSERVING, EXTEMPORANEOUSLY PREPARING, AND ADMINISTERING AN ACTIVE PRINCIPLE

The present invention relates to a device for conserving and extemporaneously preparing active principles, in particular in small doses, for administering by local or systemic injection.

The invention also seeks to use the device for extemporaneously preparing active principles with a view to administering them, in particular with a view to administering antibiotics intracamerally for preventing post-phacocystectomy infections, or to injecting ophthalmological treatments intravitreally.

Phacocystectomy is an intervention, currently practiced by hospital services and by ophthalmologists, that seeks to extract the lens of an eye that has become opaque due to a cataract and to replace it with a synthetic prosthesis.

The intervention usually consists, under local anesthetic, in making an incision in the cornea and then in the lens capsule in the front chamber of the eye, and in extracting the core of the lens after it has been fragmented by ultrasound. A foldable flexible implant is then inserted into the capsule where it is deployed in order to be centered by the operator.

Unfortunately, in spite of the usual precautions in terms of pre- and per-operative prophylaxis, phacocystectomy leads to a high number of post-operative infections that are responsible for blindness.

In order to prevent such infections, it is thus necessary at the end of intervention and before closing the front chamber of the eye, to administer an antibiotic such as cefuroxime. Health authorities recommend administering the antibiotic at a dose of 1 milligram (mg) for 0.1 milliliters (mL) of aqueous solvent.

However, antibiotics that are adapted to preventing post-phacocystectomy infections, in particular cefuroxime, are available only in doses lying in the range 250 mg to 1.5 grams (g). Such doses are too high and do not satisfy the indications of the marketing authorization for preventing post-phacocystectomy infections.

Furthermore, they quickly become unstable and cannot be prepared in advance: they should thus be put into solution only a few moments before they are administered.

Thus, administering a small dose of antibiotic, dissolved in a small volume of solvent presents great difficulties for safe implementation, in particular in terms of dose accuracy.

The hospital or private ophthalmologist, unused to regulated pharmaceutical parameters, cannot easily prepare at best a two hundred and fiftieth of a pre existing dosage form, and even less dissolve it in a small volume of aqueous solvent without being uncertain with regard to the accuracy of the dose prepared, and this not within any market authorization specific to this indication.

In order to mitigate those drawbacks, hospital pharmacies make use of freezing. Hospital pharmacies prepare appropriate doses, and then freeze them.

However, such preparations take place in-house and do not come under the regulated procedures for the manufacture and analytical inspection of industrial pharmaceutical batches, thus making any drug monitoring unreliable, even without taking account of how the dose is thawed before being administered to a patient.

In addition, conventional pharmaceutical laboratories making micro-doses of active principles and small-size containers gives rise to problems, in particular for preventing airborne and particulate contamination, and the poor stability of the active principles, and also in terms of manipulation in order to recover and dissolve the substance before using it. In parallel, opening an ampoule of physiological serum containing only 0.1 mL in order to dissolve the antibiotic, also presents difficulties in manipulation and in breaking the ampoule. In addition, the two small-size containers could easily be mixed up or misplaced.

The same problems arise in administering ophthalmological drugs intravitreally, in particular for treating pathologies of the retina. It appears that intravitreal injections, that are currently performed without the injected active principle being accompanied by an antibiotic for preventing intraocular infections, are also likely to lead to infections such as those occurring after cataract operations, and resulting in blindness.

In general, doctors encounter the same difficulties for any treatments based on unstable active principles and that can be injected intravenously, intramuscularly, subcutaneously, or even into certain organ structures, tissues, or defined cavities, e.g. substances such as peptides or active principles resulting from biotechnology.

Thus, there exists a need for a very specific device that is adapted to packaging and extemporaneously preparing unstable active principles, in particular in small doses, for administering by local or systemic injection, the device satisfying the various constraints that such packaging involves, in particular airborne contamination, stability of the active principle, and ease of manipulation.

The present invention satisfies this need by proposing a device for conserving and extemporaneously preparing at least one active principle prior to administration, the device comprising:

- a body that is constituted by at least one compartment for containing at least one volume of pharmaceutical solvent that is less than 5 mL;
- a head constituted by at least one compartment for containing at least one active principle, and, in its top portion, by at least one dose-taking chamber provided with a filter, the head being capable of taking up a first position P1 for conservation, in which said head is in its distal position relative to the body, and a second position P2 for preparation, in which said head is in its proximal position relative to the body;
- at least one wall separating the body and the head; and
- rupture means for rupturing said wall so that the active principle enters into contact with the solvent and dissolves therein.

The device makes it possible to supply a single, accurate, and controlled dose of active principle. Advantageously, it enables one or more active principles contained therein in very small doses to be dissolved almost instantaneously, and enables the dissolved active principle(s) to be taken for administering, without the need for manipulations or transfers in the outside atmosphere from one container to another, that are likely to lead to spoiling, losses, or human errors. The invention thus makes it possible to perform instantaneous mixing in a guaranteed-sterile atmosphere, without any externalization of the components involved.

It is particularly adapted to preparing and intracamerally administering antibiotics for preventing post-phacocystectomy infections, to ophthalmological treatments that can be injected intravitreally with the extemporaneous addition of antibiotics, and to any treatments based on unstable active principles that can be injected intravenously, intramuscularly, or subcutaneously, or that can even be injected into certain organ structures, tissues, or defined cavities.

The invention thus also seeks to use the device for such applications.

Other characteristics and advantages appear from the following description of the invention, which description is given merely by way of example, and with reference to the accompanying drawings, in which.

In order to make the drawings clear, the proportions are deliberately not to scale.

Figure 1:
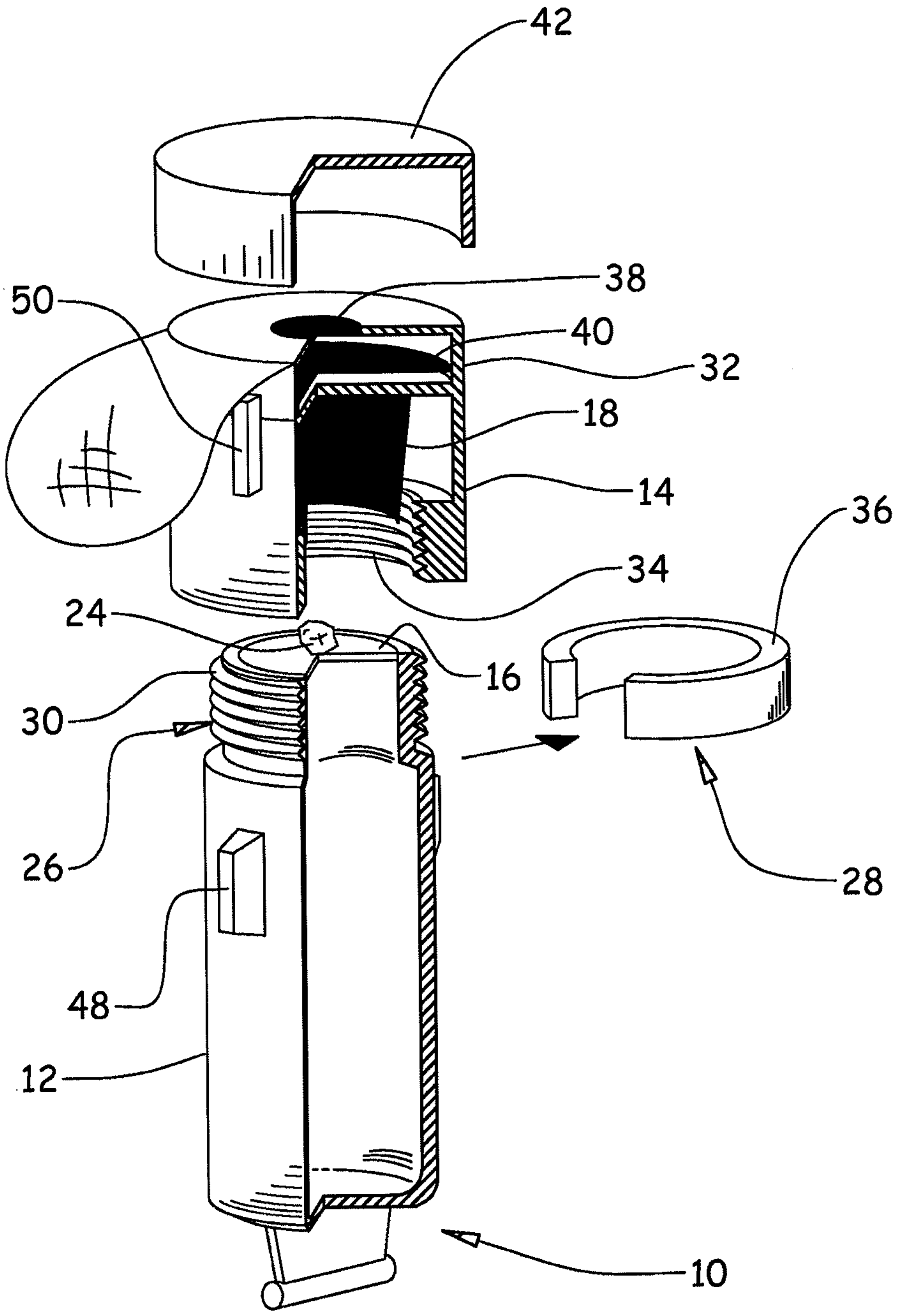
FIG. 1 is an exploded perspective view of the device of the invention.
Figure 2A:
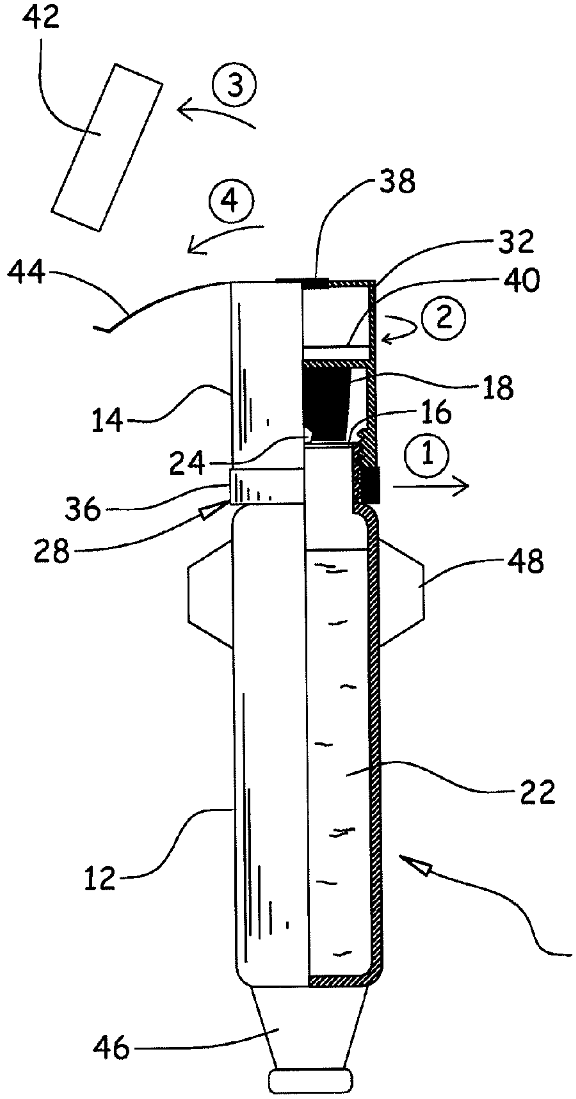
FIGS. 2A and 2B are diagrammatic views partially in section, respectively in the conservation position P1 and in the preparation position P2 prior to use.
Figure 2B:
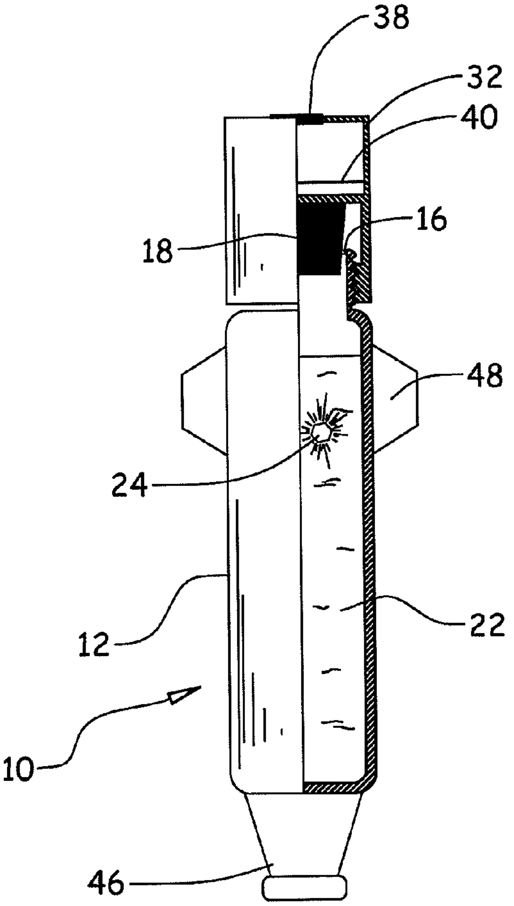

FIG. 1 shows a device 10 including a body 12 that may be made out of any material that avoids evaporation through the wall, and that is suitable for avoiding light or air acting on its contents.

Such a body is advantageously a single piece made out of thick plastics material or out of glass, that is preferably made opaque, of pharmaceutical quality, very strong, and of section that is square, oval, rectangular, triangular, or round.

The device 10 includes a head 14 that is secured to the body 12 so as to be movable relative thereto, at least in translation.

The head 14 is capable of taking up a first position P1 for conservation, in which said head 14 is in its distal position relative to the body 12, and a second position P2 for preparation, in which said head 14 is in its proximal position relative to the body 12.

The body 12 includes at least one compartment for containing a very small volume of at least one pharmaceutical solvent 22, such as physiological serum.

Preferably, the volume of solvent in a compartment is a volume that is less than 5 mL, very preferably less than 0.5 mL.

The head 14 includes at least one compartment for containing a dose of at least one active principle 24 in solid form, e.g. in the form of a lyophilisate, a powder, a tablet, or a specific polymeric gel, or in liquid form. Preferably, the active principle 24 is in powder or lyophilized form.

The dose of active principle in a compartment is preferably a dose that is less than 50 mg, preferably less than 10 mg, or even less than 5 mg.

The device of the invention is adapted to doses that vary depending on the type of active principles under consideration, their specific routes of administration, and the number of different components and compartments in the device. In particular, it is adapted to administering very small doses of active principles, but may be used for larger doses.

The term "active principle" means a substance or a combination of substances capable of producing demonstrable pharmacological activity on extra- or intra-cellular collections of tissues or of receptors, so as to reduce, prevent, or correct an acute or chronic affection or a particular degeneration.

In an embodiment, the active principle 24 is an antibiotic, even more preferably an antibiotic selected from the family of beta-lactamines, which includes cephalosporins, in particular cefuroxime or cefazolin.

The active principle 24 may also be selected from active agents that treat the pathologies of the retina, such as retinal angiopathies, retinitis, and macular degeneration associated with age. In particular, the active principle may be an intravitreal anti-angiogenic active principle such as pegaptanib sodium, bevacizumab, ranibizumab, anecortave acetate, or squalamine lactate.

The active principle may also be a labile active principle of peptide nature or resulting from biotechnology.

In its top portion, the head 14 includes at least one dose-taking chamber 32 that is provided with a filter 40 that makes it possible to avoid any particulate contamination of the dissolved active principle to be taken, by mechanically filtering the solution extracted while taking the dose. If necessary, the device may include a plurality of dose-taking chambers.

The dose-taking chamber 32 should be of appropriate size. Its length should be greater than or equal to the length of a dose-taking needle, i.e. in the range 8 mm to 40 mm, such that at the end of its stroke, a needle can never damage the filter 40.

The filter 40 preferably presents a mesh lying in the range 5 micrometers (μm) to 75 μm.

The body 12 and the head 14 of the device 10 are separated by at least one wall 16 that prevents the active principle 24 from being in contact with the solvent 22 when the head 14 is in its conservation position . The wall is preferably a metalloplastic leaktight membrane.

In a particular embodiment, the wall 16 may be associated with at least one other membrane for preventing any loss of the active principle 24 while the device is being manufactured.

The device 10 of the invention also includes rupture means 18 for rupturing the wall 16 so that the active principle 24, in solid form, enters into contact with the solvent 22 and dissolves therein.

In a preferred embodiment, the rupture means 18 are cutter means for cutting the wall 16, e.g. perforator means.

The body 12 and the head 14 are fitted with means 26, specifically a thread, for moving said head 14 in translation, from its distal position to its proximal position.

The container is also provided with safety-locking means 28 so as to prevent any involuntary movement, in translation, of the head 14 relative to the body 12.

In the preferred embodiment, the means 26 for imparting movement in translation comprise a screw thread 30 that is carried by the body 12, more particularly by the neck of the body, and tapping 34 of complementary profile to the screw thread of the container, and that is carried by the head 14 in such a manner as to co-operate by screw-fastening.

The locking means 28 comprise a removable ring 36 that is interposed between the head 14 in its distal position and the body 12.

The ring 36 has a C-shaped profile that comes to be mounted in resilient manner on the screw thread 30 that is carried by the body 12, thereby preventing the head 14 from moving in translation relative to the body 12.

In another aspect, the head 14 is provided with a perforatable membrane 38 for protecting the dose. The membrane 38 is for perforating in order to take the contents of the device 10 by means of a sterile syringe and needle.

Preferably, the membrane 38 is protected by a protective cap 42 that is held on the head 14, and by a safety tab 44.

Thus, in a sterile environment, the body 12 of the device 10 is filled with a pharmaceutical solvent 22, then the body 12 is closed in leaktight manner by putting the membrane 16 into place, and the bottom portion of the head 14 is preferably closed by at least one other membrane for preventing any loss of the active principle 24.

In a variant, the wall 16 is formed during filling of the body 12 with the solvent 22 that it is to contain in such a manner as to constitute a single dose that is sterile and sealed, and that is leaktight.

The ring 36 is disposed on the neck around the screw thread 30, then the head 14 is screwed on until it comes into abutment on the ring 36.

The dose of active principle 24 is deposited in the head 14 that, in turn, is then closed in leaktight manner by putting the membrane 38 into place.

The protective cap 42 is put into place on the head 14, thereby preventing any perforation of the membrane 38. The safety tab 44 is fitted on the head by peripheral adhesive.

In this conservation position, the packaging is not ready for use and may be conserved, without spoiling the active principle that is stable when in solid form.

When the practitioner wishes to administer the medication, it suffices for the practitioner to remove the ring 36 merely by pulling it off, and then to screw the head 14 on tighter.

The head thus moves in translation, thereby causing the rupture means 18 to tear the wall 17, then the wall 16 that provided separation between the solvent 22 and the active principle 24, thereby enabling the active principle to dissolve in the solvent. For better dissolution, it is preferable to shake the solution for a few seconds.

Removing the safety tab 44 after removing the protective cap 42 makes it possible to access the sterile membrane 38. The user needs only to perforate the membrane 38 by means of a sterile mini syringe and needle in order to take the contents of the device. Through the membrane 38, the user injects a volume of air that is greater than or equivalent to the volume of medicated solution that the user wishes to take, so as to create positive internal pressure while the liquid is being extracted, and so as to make it easier for the therapeutic solution to pass through the filter 40. By suction into the dose-taking syringe, the user recovers the desired volume of the solution contained in the device 10 and deposits said volume in the intended location, e.g. in the front chamber of the eye for preventing post-phacocystectomy infections.

The sterile needle carried by an appropriate syringe makes it possible to administer the prepared solution immediately, whatever the route of administration: intra-ophthalmic, intravenous, intramuscular, subcutaneous, intra-articular, intracavity.

Thus, the active principle is dissolved in the solvent just before it is administered, thereby preventing any premature degradation.

A single dose of active principle is administered in accurate and controlled manner.

As described above, the dimensions of the device have been maximized so as to make it possible to show the structural details as well as possible, but account should be taken of the fact that the dimensions of a container may lie in the range 0.5 mL to 2 mL, the device being extremely small and difficult to manipulate.

Thus, the present invention proposes an improvement to the container that consists in adding a grip paddle 46 that is advantageously disposed at the bottom portion of the body 12.

The grip paddle 46 makes a good two-digit pinch grip possible in spite of the small size of the container, so as to enable the user to turn the head 14.

In its top portion, the body may also present grip means (48).

In addition, on its peripheral outside surface, the head 14 may include grip means 50, such as fins.

The user is thus ready to act, by exerting torque between the body 12 and the head 14.

It should also be observed that the grip paddle 46 presents another manipulation advantage after the head has been turned relative to the body and after the protective cap 42 has been removed, namely the advantage of enabling the contents to be taken easily by means of an appropriate device.

The ring 36 may also be a plastic belt that is capable of being torn or loosened. In order to make it easier to remove the belt, an external pull tab may be added to the belt.

Figures 3A, 3B:
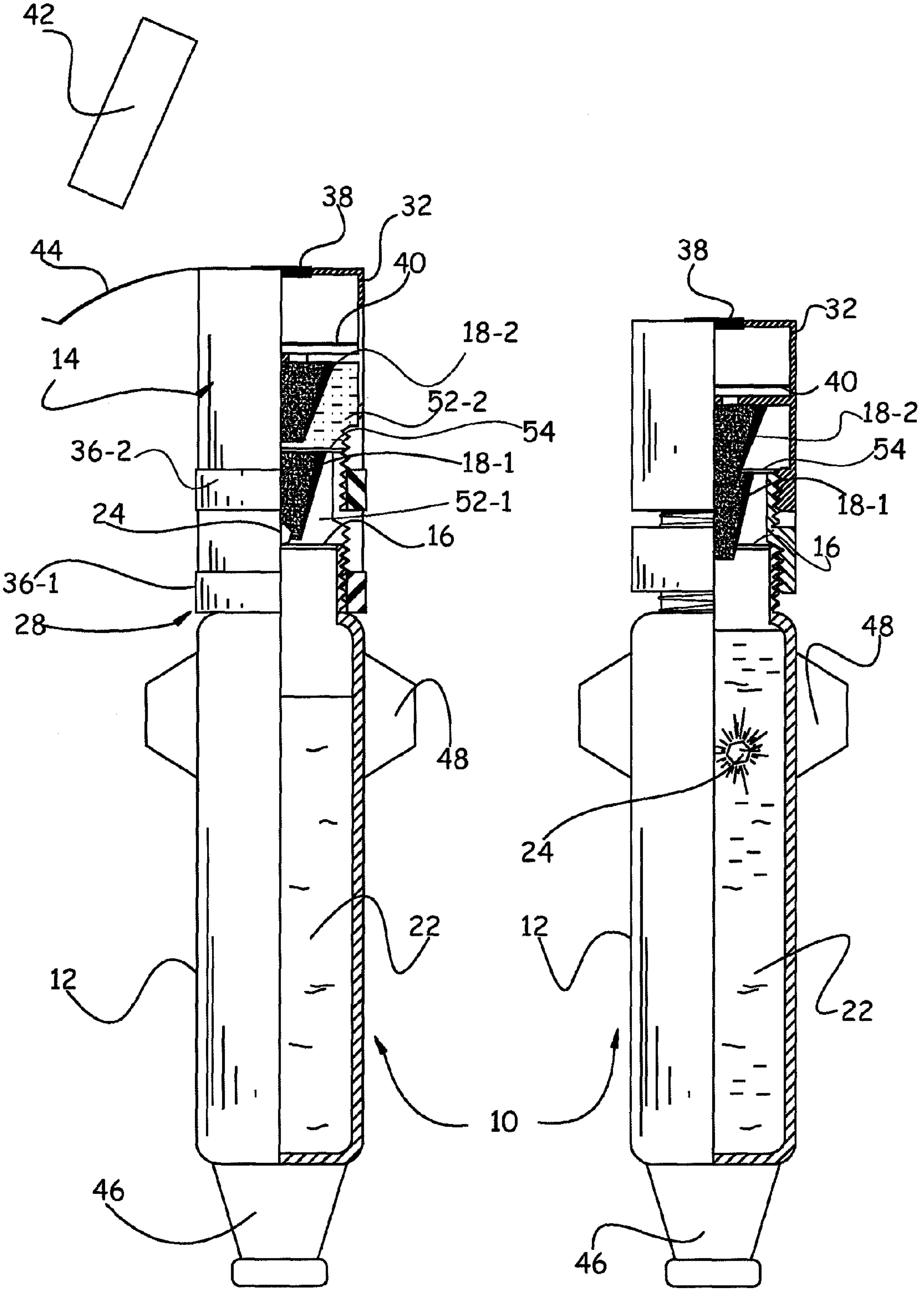
FIGS. 3A and 3B are diagrammatic views partially in section showing a variant of the invention, with a head including a plurality of compartments.

In a variant of the invention shown in FIGS. 3A and 3B, the head 14 may include at least two compartments 52-1, 52-2, the compartments being separated by at least one wall 54, and possibly by at least one additional membrane that prevents any of the contents of the compartments from being lost while the device is being manufactured. Each compartment 52-1, 52-2 contains at least an active principle, and/or an excipient, and/or a solvent, at least one compartment of the head 14 containing an active principle.

The body 12 may also include at least two compartments, each compartment being separated by at least one wall and containing at least an active principle and/or an excipient and/or a solvent, at least one of the compartments of the body 12 containing a solvent.

The device 10 may also include intermediate perforator means 18-1, 18-2 that are capable of tearing the walls that are interposed between the compartments, so as to be able to cause the substances to be mixed in a determined order.

Thus, by selectively removing the rings 36-1 and/or 36-2, followed by turning one and/or the other of the compartments, it is possible to obtain different combinations. For example, by removing the ring 36-2, the wall 54 is ruptured on turning, and the liquid of the compartment 52-2 is put into contact with the solid active principle 24 of the compartment 52-1.

Then, by removing the ring 36-1 and by additional turning, the solution that has just been formed is mixed with the contents 22 of the body 12.

Figure 4:
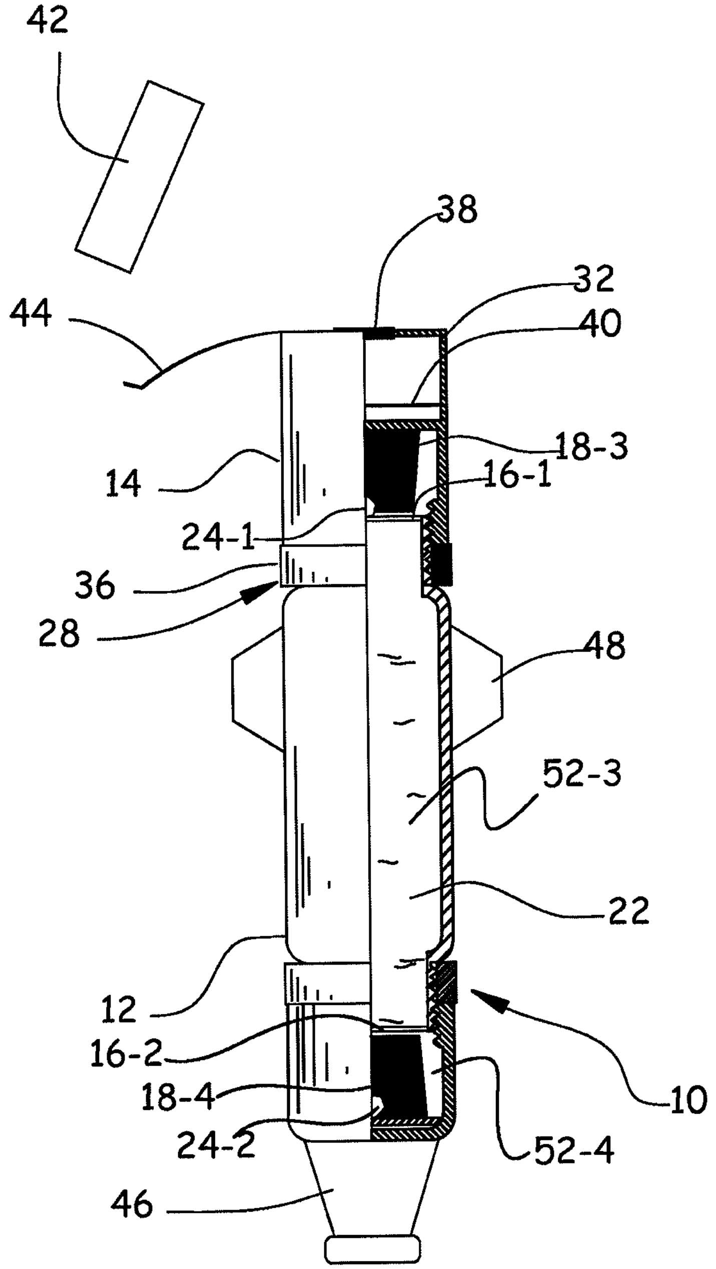
FIG. 4 is a diagrammatic view partially in section showing another variant of the invention, with a body including a plurality of compartments.

Another particular embodiment is shown in FIG. 4. In this embodiment, the body 12 of the device includes two compartments 52-3, 52-4 that are separated by at least one wall 16-2. The compartment 52-3 includes a solvent 22, and the compartment of the head 14 and the compartment 52-4 each include at least one active principle 24-1 and 24-2.

The head 14 and the compartment 52-3 of the body 12 are separated by a wall 16-1. The head 14 and the compartment 52-4 of the body 12 are also provided with rupture means 18-3 and 18-4 for rupturing the walls 16-1 and 16-2 so that the active principles 24-1 and 24-2 enter into contact with the solvent 22 and dissolve therein.

This embodiment thus makes it possible, in particular, to keep two active principles separate during their conservation, then to dissolve them, in a preferred order of a first and then a second active principle, prior to administration, e.g. such as an ophthalmic anti-angiogenic active principle and a preventive antibiotic such as cefuroxime.

Thus, the invention advantageously makes it possible to put into contact two solvents that are respectively present in contiguous compartments, and then to put this liquid mixture into contact with one or more active principles, in a given order of preparation.

In addition, it is possible to dissolve at least two active principles separately in separate adjacent solvents, and then to combine them so as to constitute a single mixture before taking the dose.

It is also possible to begin by associating at least two previously-separate active principles, then to mix them with one or more solvents.

The shapes of devices of the invention having a plurality of compartments containing a plurality of substances are particularly adapted to active principles and substances that are chemically incompatible and/or unstable in solution.

It is entirely possible to increase the number of compartments and thus the possible combinations, as a function of needs.

The device of the invention makes it possible to protect the active principle, excipient, or other substance in the form of powder, tablet, orally-disintegrating tablet, liquid microcapsule, etc. and to produce a mixture and an extemporaneous dissolution in a solvent immediately before administration. For certain components that are complex and that can spoil when left together, it is thus possible to constitute a device having a plurality of separate compartments that make it possible to combine the various poorly-compatible substances successively just before administering them, and to do this in a determined order that specifically suits their physico-chemical constitutions and sensitivities. The compartments may be assembled and disposed in any industrially-fabricated embodiment.

The device of the invention may be used for conserving and extemporaneously preparing an active principle or a mixture of active principles that is/are unstable in solution and/or chemically incompatible with a view to combining them prior to administration by injecting intravenously, intramuscularly, or subcutaneously, or even by injecting into certain organ structures, tissues, or defined cavities.

In particular, the device of the invention may be used for conserving and extemporaneously preparing antibiotics with a view to administering them intracamerally so as to prevent ocular post-phacocystectomy infections.

Another use of the device of the invention is for conserving and extemporaneously preparing ophthalmological active principles with a view to administering them by intravitreal injection, in particular in combination with antibiotics seeking to prevent intraocular infections. By way of example, the device of the invention may be used for conserving and extemporaneously preparing anti-angiogenic active principles for administering by intravitreal injection.

The device may thus contain small doses of an antibiotic for preventing endophthalmitis, such as cefuroxime, and of intravitreal anti-angiogenic active principles such as pegaptanib sodium, bevacizumab, ranibizumab, anecortave acetate, or squalamine lactate.

Thus, the device of the invention advantageously makes it possible to associate, extemporaneously, intravitreal anti-angiogenic active principles with a very small dose of labile antibiotic, such as cefuroxime, so as to prevent the intraocular infections that might result from injecting those substances. This prevention is not currently performed for intravitreal injections, but it appears to be essential in order to avoid any risk of blindness as a result of intra-ophthalmic infection associated with implementing therapeutic injections in the eye.

The invention claimed is:

1. A device for conserving and extemporaneously preparing a single injectable dose of at least one unstable active principle prior to administration, the device comprising:

a body made of thick plastic material or glass, said body comprising at least one compartment for containing at least one volume of pharmaceutical solvent that is less than 5 mL;

a head comprising at least one compartment for containing at least one active principle, and, in a top portion of the compartment, by at least one dose-taking chamber provided with a filter separating the compartment for containing the active principle from the dose-taking chamber, said head comprising a sterile perforatable membrane for protecting the dose, said device comprising a removable protective cap held on said head, the head being capable of taking up a first position P1 for conservation, in which said head is in its distal position relative to the body, and a second position P2 for preparation, in which said head is in its proximal position relative to the body;

at least one wall separating the body and the head; and a perforator for rupturing said wall so that the active principle enters into contact with the solvent and dissolves therein.

2. A device according to claim 1, wherein the device includes a screw fastener for moving the head in translation, the a screw fastener comprising a screw thread that is carried by the body, and tapping of complementary profile to the screw thread of the container, and that is carried by the head in such a manner as to co-operate by screw-fastening.

3. A device according to claim 1, wherein the device includes a safety-locking ring so as to prevent any involuntary movement, in translation, of the head relative to the body.

4. A device according to claim 3, wherein the safety locking ring comprises a removable ring that is interposed between the head in its distal position and the body.

5. A device according to claim 1, wherein the perforator for rupturing the wall has a cutter configured to tear said wall when the head is in its proximal position.

6. A device according to claim 1, wherein said protective cap is held on the head by a safety tab.

7. A device according to claim 1, wherein the device includes a grip paddle that is disposed at the bottom portion of the body, so as to make a good two-digit pinch grip possible.

8. A device according to claim 1, wherein the device includes grip fins that are disposed in the top portion of the body.

9. A device according to claim 1, wherein the head includes grip fins on a peripheral outside surface.

10. A device according to claim 1, wherein the head includes at least two compartments for containing at least one of an active principle, an excipient, and a solvent, said compartments being separated by at least one wall, and at least one of the compartments containing an active principle.

11. A device according to claim 1, wherein the body includes at least two compartments for containing at least one of an active principle, an excipient and a solvent, said compartments being separated by at least one wall, and at least one of the compartments containing a solvent.

12. A device according to claim 11, wherein the body and the head and/or each compartment of the device are separated by at least one wall and by at least one additional membrane.

13. A device according to claim 1, wherein said active principle forms part of the family of beta-lactamides.

14. A method for conserving and extemporaneously preparing at least one active principle, comprising preparing the at least one active principle for an injectable dose with the device of claim 1.

15. A method of preparing at least an antibiotic active principle that forms part of the family of beta-lactamines, comprising preparing the at least one active antibiotic principle with the device of claim 14.

16. The method of chain 14, wherein the preparing of the at least one active principle comprises combining the at least one active principle with a anti-angiogenic active principle.

17. A method of preparing at least one active principle with the device of claim 1, wherein the at least one active principle is a liable active principle comprising at least one peptide or produced using biotechnology techniques.

18. A device according to claim 1, wherein the active principle is cefuroxime or cefazolin.

19. A device for conserving and extemporaneously preparing a single injectable dose of at least one unstable active principle prior to administration, the device comprising:

a body, the body having a compartment containing at least one volume of pharmaceutical solvent;

a head having a compartment containing at least one active principle and a dose-taking chamber provided with a filter between the compartment containing the active principle from the dose taking chamber, the head having a membrane that protects the dose and configured to be perforated by a needle carried by syringe while maintaining a seal around the needle;

a removable protective cap held on the head, the head configured to take up a first position P1 for conservation, in which the head is in a distal position relative to the body, and a second position P2 for preparation, in which the head is in a proximal position relative to the body;

at least one wall separating the body and the head; and a perforator configured to rupture the wall so that the active principle enters into contact with the solvent and dissolves therein to thereby form the injectable dose of unstable active principle that is removable by the syringe and needle perforated through the membrane.

20. The device according to claim 19, comprising the active principle and the solvent that are configured to form the injectable dose of unstable active principle efficacious through injection; and wherein the membrane is sterile.

* * * * *